United States Patent [19]

Hawthorne

[11] Patent Number: 5,066,479

[45] Date of Patent: Nov. 19, 1991

[54] METALLACARBORANE CHELATES

[75] Inventor: M. Frederick Hawthorne, Los Angeles, Calif.

[73] Assignee: The Regents of the Univ. of California, Berkeley, Calif.

[21] Appl. No.: 200,750

[22] Filed: May 31, 1988

[51] Int. Cl.$^5$ .................... A61K 49/02; A61K 39/44; C07K 17/06

[52] U.S. Cl. .................. 424/1.1; 424/85.91; 424/9; 530/389; 530/390; 530/391

[58] Field of Search ............... 424/85.91, 9, 1.1; 530/389, 390, 391

[56] References Cited

U.S. PATENT DOCUMENTS

| | | | |
|---|---|---|---|
| 4,361,544 | 11/1982 | Goldenberg | 424/1.1 |
| 4,421,735 | 12/1983 | Haber et al. | 424/1.1 |
| 4,472,509 | 9/1984 | Gansow et al. | 424/1.1 |

FOREIGN PATENT DOCUMENTS

| | | | |
|---|---|---|---|
| 0188093 | 7/1986 | European Pat. Off. | 424/9 |
| 0005031 | 8/1987 | World Int. Prop. O. | 424/85.91 |

OTHER PUBLICATIONS

Meares, C. F. etal, (1984), Anal. Biochem. 142:68–78.
Gansow et al, (1984), American Chemical Society, ACS Symposium Series, No. 241, pp. 215–227.
Krecarek et al, (1977), Biochem. Biophys. Res. Comm. 77(2):581–585.
Moi et al, (1985), Anal. Biochem. 148:249–253.
J. N. Francis and M. F. Hawthorne, (1971), Synthesis and Reactions of Novel Bridged Dicarbollide Complexes Having Electron-Deficient Carbon Atoms brochure, [Reprinted from Inorganic Chemistry, 10, 594 (1971).]
J. N. Francis, C. J. Jones, and M. F. Hawthorne, (1972), "Chemistry of Bis(7,8-Dicarbollyl)Metalates". Reaction between [(-7,8-B$_9$C$_2$H$_{11}$)$_2$Co]— and Aryl Diazonium Salts brochure, [reprinted from Journal of the American Chem. Soc., 94, 4878 (1972).]
M. Frederick Hawthorne and Gary B. Dunks, Metallocarboranes That Exhibit Novel Chemical Features, American Association for the Advancement of Science, 3 Nov. 1972, vol. 178, pp. 462–471.
K. Shelly, C. B. Knobler and M. F. Hawthorne Communication, "Bridged Metalla-Bis-Dicarbollides: Structure of [10,10'-u-(1,2-C$_6$H$_4$)-bis-(7,8-C$_2$B$_9$H$_{10}$)$_2$-]Co (1-) and Synthesis of Its Iron Analog", New J. Chem., 1988, 1, (3 pages).

Primary Examiner—Jeffrey E. Russel
Assistant Examiner—Kay Kim
Attorney, Agent, or Firm—Poms, Smith, Lande & Rose

[57] ABSTRACT

Metallacarborane chelate-antibody compounds which are useful for radioimmunodetection and radiotherapy. The compounds have the formula

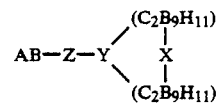

wherein X is a metal or radioisotope of said metal, Y is a rotation resistant organic chelate bridge moiety, Z is an antibody linkage moiety and AB is an antibody. Metallacarborane chelate and carborane chelate compounds are also disclosed which are useful in preparing the final metallacarborane chelate-antibody compound which is used for radioimmunodetection and radiotherapy.

11 Claims, 4 Drawing Sheets

○ BH
● CH
⊖ B
⊘ N
● Co⁺³ d- or l-8      meso-8

○ BH
● CH
⊖ B

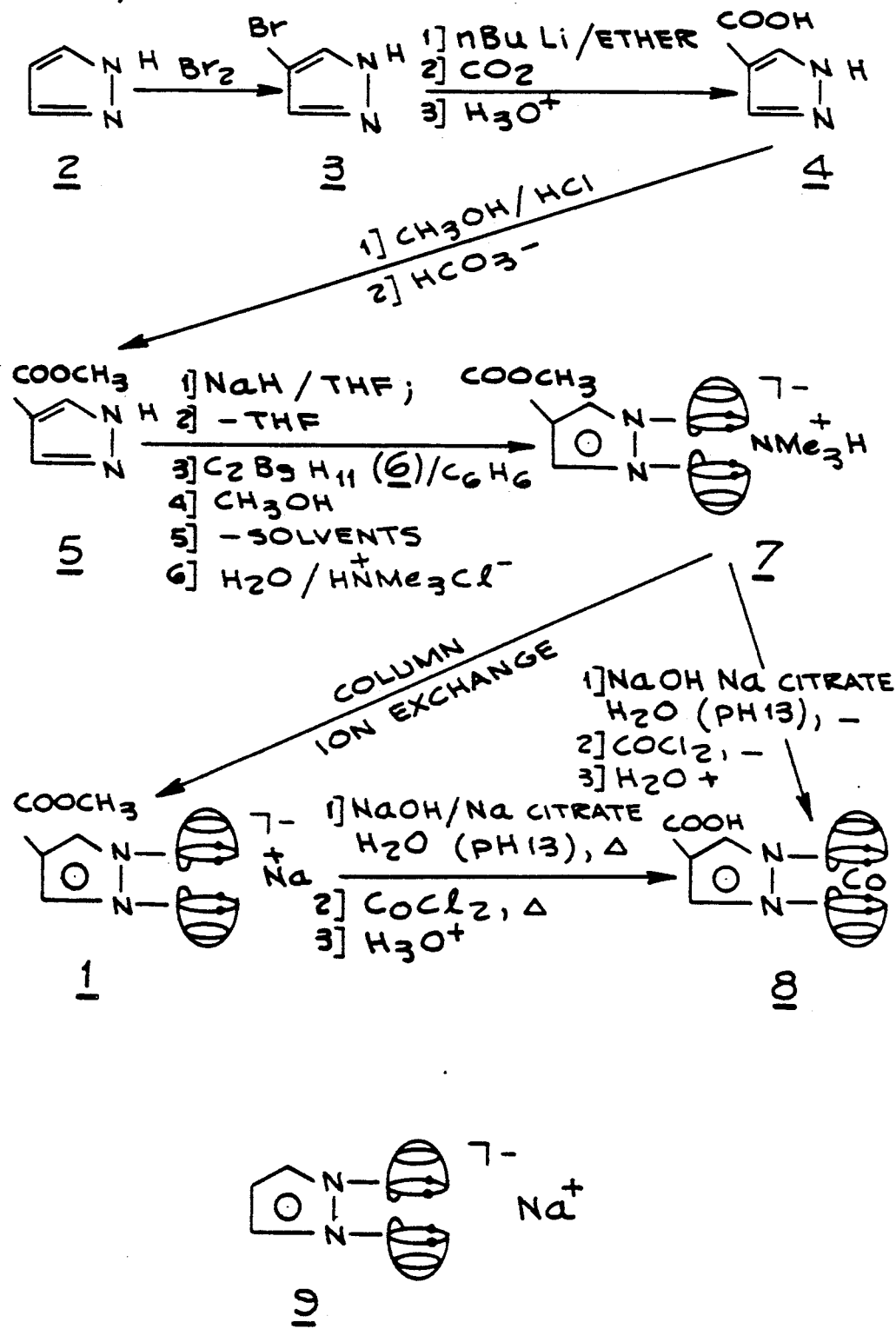

METALLACARBORANE CHELATES

This invention was made with Government support under Grant No. Ca-31753 awarded by the Department of Health and Human Services. The Government has certain rights in this invention.

BACKGROUND OF THE INVENTION

1. Field of the Invention

The present invention relates generally to radioimmunodetection and radiotherapy of diseases such as cancer. More particularly, the present invention relates to the chemicals used in transporting radio-isotopes to the tumor or organ which is being imaged and/or treated.

2. Description of Related Art

There presently is great interest in the use of radioisotopes in gamma imaging and/or beta therapy of cancer. These procedures basically involve conjugating the radioisotope or radiometal to a tumor-specific or tumor-associated antibody. Upon administration to the vascular system, the antibody-radioisotope conjugate attaches only to the specific tumor of interest. Radioimaging or radiotherapy can then be accomplished at the tumor depending upon which radioisotope is used.

At the present time, radioimmunodetection of cancer is practiced using $^{111}$In, $^{99m}$Tc, $^{68}$Ga and other short lived radioisotopes in combination with bifunctional organic molecules capable of chelating the radiometal ion and conjugating with a tumor-associated or tumor-specific antibody. While this imaging methodology is a potentially powerful tool, it has not yet been developed to the fullest extent possible The principal difficulty is the innate chemical instability of the organic chelates when subjected to the physiological conditions encountered in vivo. Thus, radiometals often break away from decomposed chelate and are deposited in the liver, spleen, bone marrow, etc. This decomposition of the organic chelates is undesirable because it not only reduces effectiveness of the treatment, but also prevents rapid excretion of excess radioisotopes from the body.

It would be desirable to provide improved chelate molecules which can be used to transport radiometals to specific tumors or organs without the problems of decomposition associated with the use of organic chelates.

SUMMARY OF THE INVENTION

In accordance with the present invention, an inorganic chelate is disclosed which is suitable for conjugation with a tumor-specific antibody for transporting radiometals to tumors or other organs for radioimaging and/or radiotherapy. The inorganic nature of the chelate makes it resistant to physiological attack in vivo and the stability of the inorganic chelate insures transport of the radioisotope to the specific tumor. The resistance of the inorganic chelate to attack by the physiologic system prevents degradation of the molecule and promotes rapid excretion of excess metal complex from the system.

The present invention is based on the discovery that chelated commo-bis-dicarbollide complexes of metals and radiometals can be conjugated with antibodies to provide a useful means for transporting radioisotopes to specific antigenic sites or tumors for radioimmunodetection and/or radiotherapy.

The metallacarborane chelate-antibody compounds in accordance with the present invention have the formula

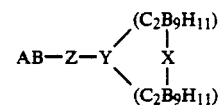

wherein X is a metal or radioisotope of said metal, Y is a rotation resistant organic chelate bridge moiety, Z is an antibody linkage moiety and AB is an antibody. These metallacarborane chelates are not organic chelates and therefore are resistant to attack by the physiologic system. As a feature of the present invention, the radiometals complexed or chelated with the dicarbollide complex are transition metals having d-electrons available for pi-bonding with the carborane ligands. Such radiometals include radioisotopes of Tc, Co, Cu, Rh, Re and many others which emit useful gamma radiation, beta particles or both.

$^{99m}$Tc is an excellent radiometal which is useful in radiodetection. However, wide use of $^{99m}$Tc has not been realized in antibody mediated imaging due to limitations in the currently known chelate systems based upon common EDTA-like organic ligands. As a feature of the present invention, incorporation of $^{99m}$Tc with the dicarbollide chelate is possible resulting in the formation of a stable complex which is useful in transporting the $^{99m}$Tc to tumor-specific sites.

As another feature of the present invention, metallacarborane chelates are disclosed which can be used in preparing the final metallacarborane chelate-antibody compounds. The metallacarborane chelate has the formula

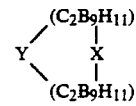

wherein X is a metal or radioisotope of said metal and Y is a rotation resistant organic chelate bridge moiety. These metallacarborane chelates are useful because they can be prepared first and then stored for later conjugation to desired antibodies. The final product is a metallacarborane chelate-antibody compound which provides an extremely stable transport vehicle for introducing radiometals to specific antigenic sites within the body.

The above-described and many other features and attendant advantages of the present invention will become better understood by reference to the following detailed description when considered in conjunction with the accompanying drawings.

BRIEF DESCRIPTION OF THE DRAWINGS

FIG. 7 is a diagrammatic representation of exemplary methods for attaching functional groups capable of bonding to antibodies to the precursor of the chelate bridge moiety (Y) of the metallacarborane and/or carborane chelates.

DESCRIPTION OF THE PREFERRED EMBODIMENT

Figure 1:
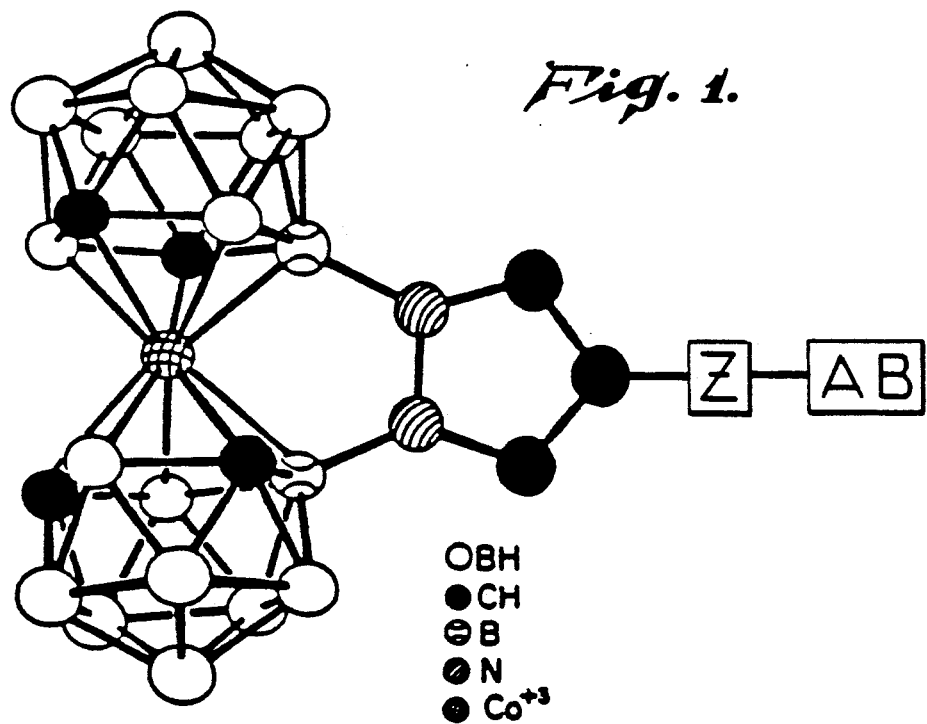
FIG. 1 is a structural representation of a preferred metallacarborane chelate-antibody compound in accordance with the present invention.

The present invention involves the synthesis and reactions of bridged dicarbollide complexes which are especially well suited for chelation with metals or radiometals useful in radioimmunodetection and radiotherapy and conjugation to antibodies.

Although the compounds in accordance with the present invention are especially well suited for use in radioimmunodetection and radiotherapy of cancer, the compounds may be used in a wide variety of radioimaging and/or radiotherapy procedures wherein it is desirable to have metal or radiometals transported to specific sites within the body. The following description will be limited to a discussion of the metallacarborane chelate-antibody compounds for use in radioimaging and radiotherapy of tumors with it being understood that the use of these compounds is not limited to these techniques.

The metallacarborane chelate-antibody compound in accordance with the present invention has the formula

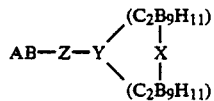

wherein X is a metal or radioisotope of said metal, Y is a rotation resistant organic bridge chelate moiety, Z is an antibody linkage moiety and AB is an antibody.

Suitable metals include Mn, Tc, Re, Fe, Ru, Os, Co, Rh, Ir, Ni, Pd, Pt, Cu, Ag, Au and radioisotopes of these metals. Preferred radioisotopes include $^{57}Co$, $^{99m}Tc$, $^{67}Cu$, $^{186}Re$ and $^{105}Rh$.

Suitable rotation resistant organic chelate bridge moieties include moieties having from 1 to 3 carbon atoms, hydrazine and cyclic hydrazine derivatives. The chelate bridge moiety is preferably resistant to molecular rotation in order to provide proper positioning of the dicarbollide ligands. The chelate bridge moiety must also be of sufficient size, shape and have the required bonding sites to provide proper orientation of the dicarbollide ligands. Preferred bridge moieties include cyclic compounds such as 1,2-phenylene, 1,2-pyrazolylene and 1,2-cyclopentadienylene. Other suitable chelate bridge moieties include alkyl or aryl carboxylates and dithiocarboxylates. Examples include formate, dithioformate, acetate and other properly substituted cis-1,2,-ethylene compounds. Exemplary synthesis of metallacarborane chelates using various of the above-described chelate bridge moieties have been previously described. (Francis J. N., Hawthorne M. F., Inorganic Chemistry, 10, 594, 1971; and Francis J. N., Jones C. J. and Hawthorne M. F., Journal of American Chemical Society, 94, 4878, 1972). It should be noted that in accordance with the present invention, it is preferred to first prepare the carborane cages linked together by the organic chelate bridge and then insert the metal into the chelate structure. 1,2-phenylene and 1,2-pyrazolylene are particularly preferred chelate bridge moieties because they provide desired dicarbollide linkage positioning as well as providing an optimum location for linkage of an antibody to the chelate complex.

The antibody linkage moiety (Z) may be any of the short chain carbon moieties typically used in linking antibodies to various molecules. These include isocyanate, isothiocyanate, carboxyl and amino groups. These linkages are used to form the connection between the antibody and the chelate bridge moiety. The use of such linking moieties is well-known and has been conventionally used in conjugating antibodies to a wide variety of molecules.

The particular antibody which is conjugated to the metallacarborane chelate can vary widely depending upon the specific tumor or antigenic site being targeted. Preferably, the antibody is a monoclonal antibody to insure specific targeting of the metallacarborane chelate compound.

A preferred exemplary metallacarborane chelate-antibody compound in accordance with the present invention is shown in FIG. 1. For this particular compound, X is cobalt and Y is 1,2-phenylene. Z and AB can be any of the known antibody linkage and antibodies previously mentioned. For this particular compound, the net overall charge is −1. However, the net charge for other metallacarborane chelates will vary depending upon the particular metal or bridging moiety used. Positively charged structures are not stable. Most of the chelates will have net charges of between −3 and 0.

Figure 2:
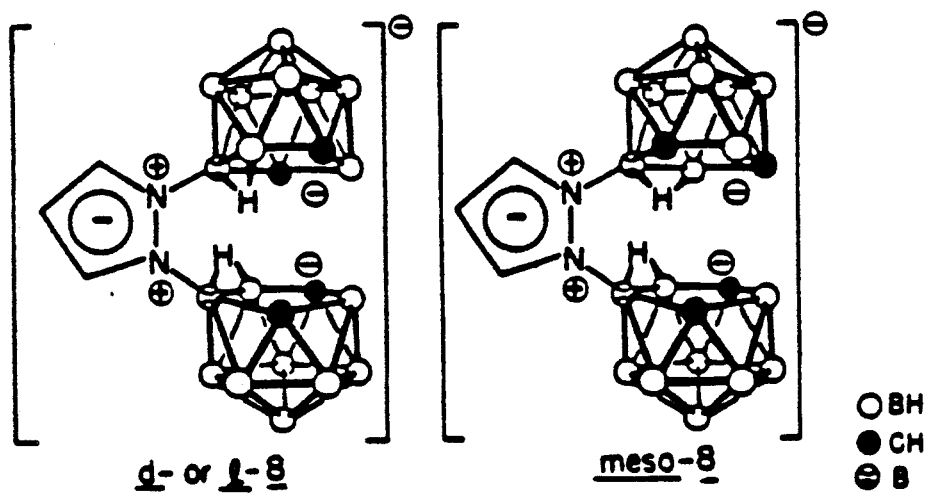
FIG. 2 is a molecular representation of isomers of a preferred carborane chelate prior to incorporation of the transition metal therein.
Figure 3:
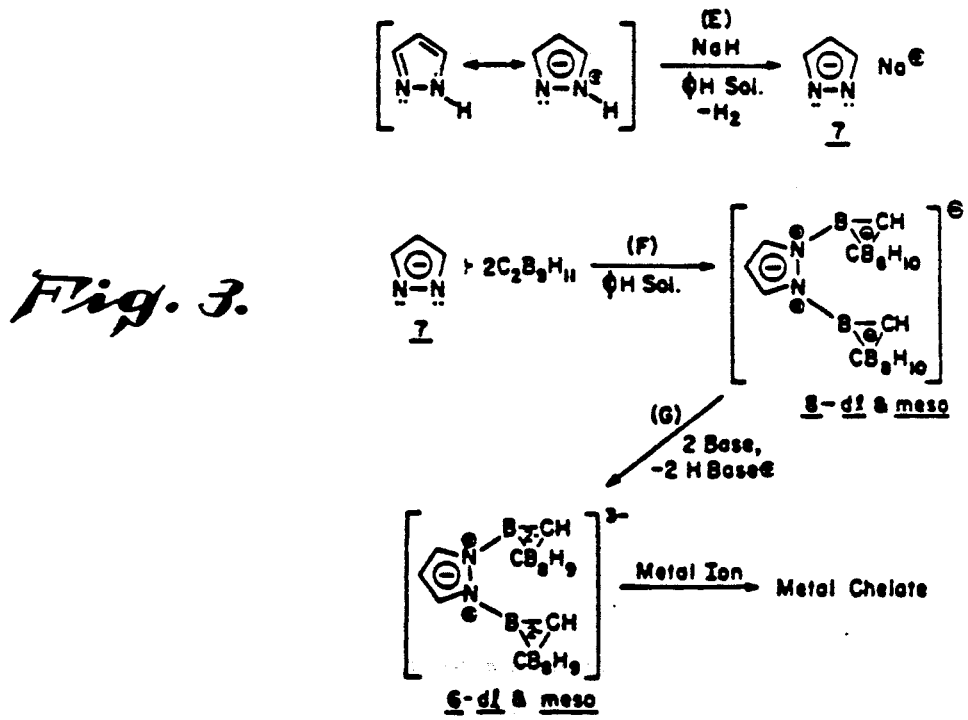
FIG. 3 is a schematic representation of the synthesis of the compounds shown in FIGS. 1 and 2.

The synthesis of the metallacarborane chelate portion of the conjugate shown in FIG. 1 is pictorially represented in FIG. 3. The structure of the intermediate carborane chelate 8 is shown in FIG. 2. The synthesis initially involves reacting pyrazole with sodium hydride in benzene (E). This is a brisk reaction and produces a high yield of the sodium salt of pyrazole 7. Two moles of closo-$C_2B_9H_{11}$ per mole of 7 produces in situ, via step (F) the anion 8 which is shown in FIG. 2. The yield from this step is approximately 90 percent. The sodium salt of 8 can be extracted from the reaction mixture with water and the anion 8 precipitated as the tetramethylammonium salt.

Two types of isomers of anion 8 are produced in approximately equal amounts: a meso-isomer and a dl, isomer. The isomers may be separated by fractional crystallization of a crude mixture of their tetramethylammonium salts from acetonitrile/water.

The conversion of either isomer of 8 to the corresponding isomer 6 of shown in FIG. 3 can be accomplished without carborane cage isomerization utilizing aqueous base as indicated in step (G). Such an aqueous procedure has been used in the past (M. F. Hawthorne, Accts. Chem. Res., 1968, 1, 281 and M. F. Hawthorne and G. B. Dunks, Science, 1972, 178, 462) for the preparation of commo-transition metal bis-dicarbollide complexes. In this known procedure, concentrated hydroxide ion solutions are employed.

Alternatively, $CoCl_2$ in phosphate buffer solutions of the sodium salt of Compound 8 (mixture of isomers shown in FIG. 3) at 0° C. and at pH 10 or at pH 12 also gives good yields of isomeric $Co^{+3}$ chelates of Compound 6. Reaction at pH 10 was completed after about six hours while at pH 12 the reaction was completed soon after mixing the reagents. Although $Co^{+2}$ (as the chloride) was used as the cobalt source, air-oxidation of the reaction mixture afforded the two isomeric and very stable $Co^{+3}$ chelates. The two isomers of the cobalt chelate were neutral species soluble in non-polar solvents and easily separated by conventional column chromatography using alumina as the absorbent and benzene/hexane as the eluting solvent. Both isomers of the cobalt chelate of Compound 6 were characterized by 500 MHz$^1$HFTNMR spectra. The chelates were subjected to crystal growth procedures and a single crystal of what proved to be the dl-isomer was selected for an X-ray diffraction study. This study confirmed that the structure of the cobalt chelate of Compound 6 is that shown in FIG. 1 prior to attachment of the antibody AB and required antibody linkage moiety Z.

Metallacarborane chelates having structures the same as shown in FIG. 1 wherein the chelated metals were $Cu^{+3}$ and $Ni^{+3}$ were also made according to the same general procedure previously described and depicted in FIG. 3.

Figure 6:
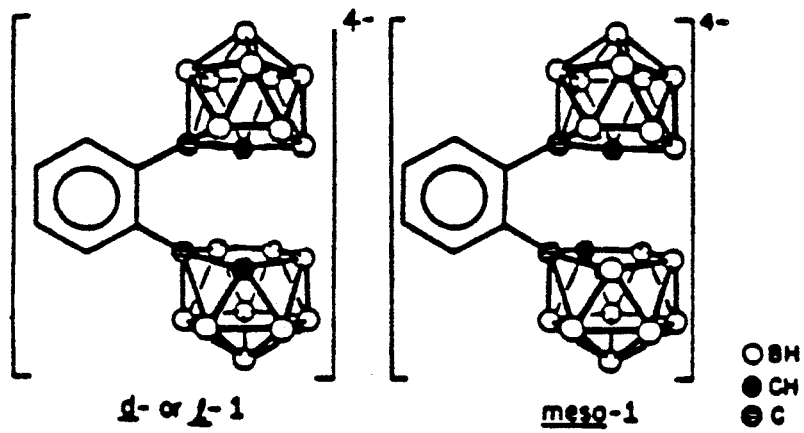
FIG. 6 is a molecular representation of a second preferred carborane chelate complex.

FIG. 6 depicts an alternate exemplary carborane chelate which is suitable for chelation with a metal or radiometal and conjugation to an antibody. The carborane chelate shown in FIG. 6 is identified as Compound 1 and is similar to Compound 8 shown in FIG. 2 except that benzene is substituted for pyrazole as the chelate bridge moiety and attachment to the carborane ligands is at a carbon atom on the carborane cage instead at a boron atom (see FIGS. 2 and 6).

Figure 5:
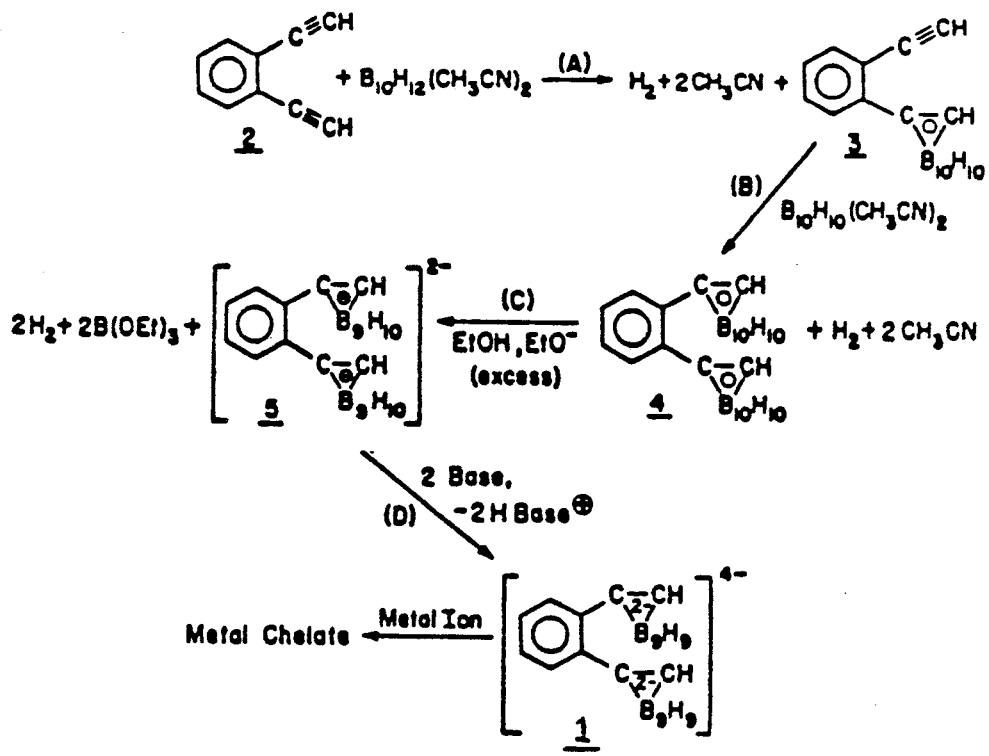
FIG. 5 is a diagrammatic representation of the synthesis of a second preferred metallacarborane chelate.

A schematic representation of the process for synthesizing metal chelates of Compound 1 is set forth in FIG. 5. Referring to FIG. 5, steps (A) and (B) are conventional reactions which lead to carborane formation. Step (C) is the well-known base degradation of an icosahedral carborane (closo-1,2-$C_2B_{10}H_{12}$) to the corresponding (7,8-$C_2B_9H_{12}$)- ion while step (D) involves the removal of the B-H-B bridge hydrogen atoms present in each of the substituted (7,8-$C_2B_9H_{12}$)- moieties contained in Compound 5 as protons. This latter step forms the desired tetranion Compound 1 which is then complexed with the desired metal or radiometal ion in situ. Although actual synthesis of Compound 3 proceeded with a 60 percent yield, the reaction of step (B) to produce Compound 4 had relatively low yields. Accordingly, although a preferred metallacarborane chelate can be made using this synthesis route, the yields are not as high as those experienced utilizing pyrazole as the chelate bridge moiety.

Figure 4:
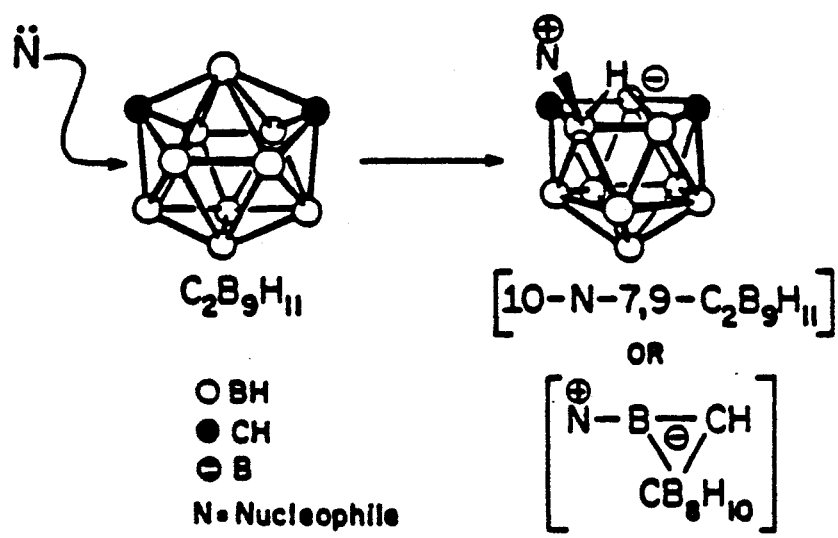
FIG. 4 is a diagrammatic representation of the course of the reaction used to form the carborane ligands.

The reaction of the polyhedral carborane, closo-$C_2B_9H_{11}$, with a variety of nucleophiles to produce B-substituted derivatives of the (7,9-$C_2B_9H_{12}$)- ion have been reported (F. N. Tebbe, P. M. Garret and M. F. Hawthorne, J. Am. Chem. Soc., 1964, 86, 4222 and F. N. Tebbe, P. M. Garret and M. F. Hawthorne, J. Am. Chem. Soc., 1968, 90, 869). The structural configuration of the carborane ligands during this reaction is illustrated in FIG. 4 and, as previously discussed, results in the production of a species having a net charge equal to that of the nucleophile. FIG. 4 also describes the carborane symbols that are used in the synthesis schemes set forth in FIGS. 3 and 5.

It is generally preferred to prepare the carborane chelate as shown in FIGS. 2 or 6 and then form the metallacarborane chelate. Once the metallacarborane chelate is formed, then it can be conjugated with a suitable antibody, such as monoclonal antibody to form the final metallacarborane chelate-antibody compound. The procedure for conjugating an antibody to the metallacarborane chelate can be any of the well-known methods for conjugating antibodies to conventional carrier molecules.

The metallacarborane-antibody compounds are especially well suited for use in radioimmunodetection and/or radiotherapy when metallic isotopes are used. However, these compounds may also be used in connection with boron neutron capture therapy. In this type of therapy, the metallacarborane-antibody compound will include a non-radioactive metal and boron serves as a thermoneutron target for use in boron neutron capture therapy. The procedures used in boron neutron capture therapy are well-known and do not form part of the invention other than the non-radioactive metallacarborane-antibody compound in accordance with the present invention may be used in such procedures.

An additional example of preparation of preferred exemplary compounds in accordance with the present invention is set forth in FIG. 7. The compounds in FIG. 7 are identified by numbers which will be referred to in the following description. The example involves the synthesis of a cobalt complex of the ligand 4-carboxypyrazole-bis-dicarbolide (1) and the conjugation of the $^{57}$Co complex of (1) to monoclonal antibodies.

For those reactions that required exclusion of air and moisture, manipulations were carried out under an atmosphere of high purity nitrogen using standard Schlenk apparatus and techniques. Where indicated, solvents were dried and purified by distillation under nitrogen using appropriate drying agents. The following chemicals were commercially available: $CoCl_2$ (Fisher Scientific Company); NaH, pyrazole, and trimethylammonium chloride (Aldrich Chemical Company); n-butyllithium (Ventron Alfa Products) 57$CoCl_2$ (ICN). The monoclonal anti-CEA antibody T84-66 was provided by Beckman Research Institute of the City of Hope.

Referring to FIG. 7, the syntheses of 4-bromopyrazole (3), 4-carboxypyrazole (4), 4-carbomethoxypyrazole (5), and closo-$C_2B_9H_{11}$(6), were based on methods previously reported in the literature, with proper modifications. J, Elguero and R. Jacquier, Bull.Soc.Chim.Fr., 2832 (1966); R. Hiittel and M. E. Schon, Liebigs Ann. Chem., 625, 55, (1959); R. A. Jones, J.Am.Chem.Soc., 71, 3994 (1949); F. N. Tebbe, P. M. Garrett and M. F. Hawthorne, J.Am.Chem.Soc., 90, 269 (1968); N. Kevin, M. Sc. Thesis, University of California, Los Angeles, March 1988.

The ligand (1) was synthesized for the first time. The parent compound which is shown at 9 (which does not possess the carbomethoxy substituent) has also been prepared.

A detailed description of the synthesis shown in FIG. 7 is as follows:

1. Preparation of 4-bromopyrazole (3):

To a solution of pyrazole (2) (10 g, 0.15 m) in glacial acetic acid (30 ml) was added a solution of bromine (8.5 ml, 0.165 m) in acetic acid (20 ml) slowly over a period of 5 hours. The mixture was diluted with acetic acid (90 ml) and allowed to stir for 6 hours. The solid obtained was filtered off. Further crops of the solid were obtained by the successive addition of petroleum ether to the filtrate, followed by filtration. The solids were combined, washed with petroleum ether and dried. The solid was dissolved in water, carefully neutralized with sodium bicarbonate and extracted with ether (4×100 ml). The ether solution was dried over $MgSO_4$, filtered and concentrated. 4-bromopyrazole (3) obtained as a white solid.

2. Preparation of Pyrazole -4-carboxylic acid (4):

To a solution 4-bromopyrazole (3) (3.82 g, 0.026 m) in ether (30 ml) at −78° C., was added a solution of 2-4 M n-butyllithium in hexane (21.7 ml, 0.052 m) in drops over a period of 40 minutes. After stirring at −78° C. for 3½ hours, the solution was warmed to ambient temperature and stirred for a further period of 5 hours. The solution was cooled again to −78° C. and excess dry ice was added. After stirring for 2 hours at −78° C., the reaction mixture was allowed to warm to ambient temperature overnight. Water was added to quench the reaction and the heterogeneous mixture was neutralized to ph 7 by the careful addition of concentrated HCl. The mixture was further diluted with water to dissolve all the solids and was washed with ether. Water was removed from the aqueous layer by distillation under vacuum to yield an off-white solid (4.38 g, crude 4). The product was not purified and was carried on for the subsequent reaction.

3. Preparation of 4-carbomethoxypyrazole (5):

To an ice cold saturated solution of HCl in methanol (500 ml), pyrazole-4-carboxylic acid (4) (19.2 g, 0.17 m) was added and the solution stirred at 0° C. for 3 hours and at ambient temperature overnight. The solvent was distilled off and the brown residue was dissolved in water. The aqueous solution was neutralized with $NaHCO_3$ and the product was repeatedly extracted with ether (25×100 ml). The ether extract was dried over Mg $SO_4$ and concentrated to give the methyl ester (5) as a pale yellow solid (13.59 g, 79.6%).

4. Preparation 4-carbomethoxypyrazoryl-bis-dicarbollide sodium salt 1:

closo-$C_2B_9H_{11}$ (6) was prepared according to the literature method (F. N. Tebbe, P. M. Garrett and M. F. Hawthorne, J. Am. Chem. Soc., 90, 269 (1968); N. Kevin, M. Sc. Thesis, University of California, Los Angeles, March 1988). To a suspension of NaH (0.144 g, 6 mm) in dry THF (10 ml) was added a solution of the methyl ester (5) (0.252 g, 2 mm) in dry THF (30 ml) under a nitrogen atmosphere. After the brisk effervescence had subsided, the mixture was stirred overnight at ambient temperature. The solvent was removed under vacuum and to the dry solid benzene (25 ml) was added and stirred. Addition of a solution of closo-$C_2B_9H_{11}$ (6) (0.794 g, 3 mm) in dry benzene (75 ml) was followed by stirring overnight at ambient temperature. Dry ether (60 ml) was added and the mixture stirred for a further period of 24 hours. The excess NaH was quenched by the careful addition of $CH_3OH$ and the solvent was removed by rotary evaporation. Drying under vacuum yielded a white solid, which was dissolved in water and the solution filtered. Addition of a solution of trimethylammonium chloride (5 g) in water (25 ml) precipitated the trimethylammonium salt-(7) as a mixture of diastereomers which was filtered and dried under suction overnight. The solid was re-dissolved in acetone and filtered. Concentration of the filtrate yielded (7) as a fluffy white solid. The crude product weighed 0.9 g (100%).

The sodium salt (1) was prepared by ion-exchange chromatography on Biorad AG 50W cation exchange resin ($Na^+$ form, 20–50 mesh) using 60:40 acetone/water mixture as the eluate. The eluate was concentrated, filtered and dried under vacuum to yield (1) as a white solid. Due to its hygroscopic nature, (1) was stored in a vacuum desiccator.

5. Preparation of Cobalt Complex of 4-carbo-methoxypyrazolyl-bis-dicarbollide (8):

To a solution of NaOH (0.8 g, 20 mm) and sodium citrate (0.53 g, 1.82 mm) in $H_2O$ (30 ml, pH 13) (7) (0.1 g, 0.22 mm) was added and the solution kept at 100° C. for 5 minutes. Then the mixture was kept under reduced pressure (20 mm) at ambient temperature for 15 minutes to remove the trimethylamine formed. Addition of $CoCl_2 \cdot 6H_2O$ (0.21 g, 0.9 mm) was followed by stirring at ambient temperature for 25 minutes. The mixture was heated at 100° C. for 15 minutes, cooled to room temperature and cooled in ice. The mixture was acidified with concentrated HCl and the product was extracted into $CH_2Cl_2$. The organic layer was washed with water, dried over $Na_2SO_4$, filtered and concentrated to obtain the crude product (8) as an orange-yellow solid (48.2mg; 50%). The product (8) was obtained as a mixture of diastereomers along with an impurity, tentatively identified as $C_2B_7H_{13}$. Repeated dissolution in ether, filtration and concentration, resulted in the removal of this impurity. The sodium salt 1 can also be employed in this reaction.

6. Synthesis of $^{57}Co$-(8) and Conjugation to Anti-CEA Mab T84.66:

The sodium salt 1 (25 mg, 609 μm) was dissolved in 2 ml 40% NaOH with heating. $^{57}Co$, as $CoCl_2$ (2.55 mc$_i$, 0.0064 μm) was added to the solution and it was heated to boiling for 30 minutes. After cooling to 0° C., the solution was neutralized with concentrated HCl. The precipitated $^{57}Co$-(8) was extracted into ether, the ether extract dried over $Na_2SO_4$ and concentrated. The complex $^{57}Co$-(8) was then redissolved in acetonitrile (600 μl) and used for subsequent conjugation to the antibody.

Approximately 50% of the radioactivity was contained in the ether extract. Based on this it was assumed that approximately 30 μm of $^{57}Co$-(8) was produced. This value is probably high because some of the compound was lost during the evaporation of ether and the subsequent dissolution in acetonitrile.

The N-hydroxysuccinimide (NHS) active ester of $^{57}Co$-(8) was prepared using diisopropylcarbodiimide, however, that compound precipitated out when added to an aqueous solution of the antibody.

A second synthesis of an active ester was carried out as follows: $^{57}Co$-(8) (2.5 μm, 50 μl) was diluted with an equal volume of water. N-hydroxysulfosuccinimide (10 μm in 50%, acetonitrile, 20 μl) and ethyldiaminopropylcarbodimide hydrochloride (EDC, 10 μm in 50% aqueous acetonitrile, 10 μl) were added and the mixture stirred for 30 minutes at ambient temperature. Various amounts of the active ester solution were added to the anti-CEA Mab solution (5 mg/ml in phosphate buffer, pH 7.5, 100 μl). The solutions were vortexed vigorously and incubated at ambient temperature for 30 minutes. As a control, unactivated $^{57}Co$-(8) (10 μl) was added to an equivalent amount of the antibody. The conjugates were purified using sephadex A-50 fine centrifuge columns 0.15 m citrate (pH 6.5) as the elution buffer. Two hours after the first purification, the conjugates were re-purified using the same method.

The results are summarized in the following table. Each conjugation mixture was counted before, after the first and the second purification using 3 μl aliquots CPM/3 μl and the percentages relative to the prepurification value are presented below.

| Sample | Vol. | Before Purification | After first Purification | After second Purification |
|---|---|---|---|---|
| Control | 10 μl | 485820 | 84510 (17.3%) | 38970 (8.0%) |
| Conjugate | 2 μl | 92900 | 34240 (36.9%) | 23280 (25.1%) |
| Conjugate | 5 μl | 207050 | 104300 (50.4%) | 75250 (36.3%) |
| Conjugate | 10 μl | 407100 | 190000 (46.7%) | 183350 (45.0%) |
| Conjugate | 20 μl | 805530 | 526350 (65.3%) | 446430 (55.4%) |

The results indicate that though there is some nonspecific binding of the $^{57}Co$ complex to the antibody, there is significant covalent binding of the labeled complex. These results demonstrate the feasibility of covalently attaching sandwich complexes of radiometals to antibodies for diagnostics and therapy.

The metallacarborane-antibody compounds in accordance with the present invention are administered to the patient or test animal by any of the conventional techniques utilized for introducing such radio imaging or radiotherapy compounds. The compound is preferably administered as an aqueous (saline) solution which is injected intravenously. The dosage of metallacarborane-antibody compound will vary widely depending upon the metallic isotope being used, the specific antibody and the type of tumor being imaged or treated and the particular therapy or diagnostic procedure. The dosage levels will be similar to those currently used for related antibody mediated tumor imaging and radiotherapy. Other suitable pharmaceutical carriers can be used if desired; however, aqueous solutions are preferred.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A metallocarborane chelate-antibody compound having a formula

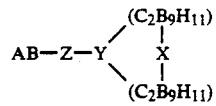

wherein X is a metal selected from the group consisting of Mn, Tc, Re, Fe, Ru, Os, Co, Rh, Ir, Ni, Pd, Pt, Cu, Ag and Au, Y is a rotation resistant organic chelate bridge moiety, Z is an antibody linkage moiety and AB is an antibody.

2. A metallacarborane chelate-antibody compound according to claim 1 wherein X is a radioisotope of a metal selected from the group consisting of Mn, Tc, Re, Fe, Ru, Os, Co, Rh, Ir, Ni, Pd, Pt, Cu, Ag, and Au.

3. A metallacarborane chelate-antibody compound according to claim 1 wherein Y is selected from the group consisting of 1,2-phenylene, 1,2-pyrazolylene, 1,2-cyclopentadienylene, formate, dithioformate and acetate.

4. A metallacarborane chelate-antibody compound according to claim 1 wherein Z is selected from the group consisting of isocyanate, isothiocyanate, carboxyl and amino groups.

5. A metallacarbone chelate-antibody compound according to claim 1 wherein AB is a monoclonal antibody.

6. A metallacarborane chelate-antibody compound according to claim 1 wherein Y is 1,2-phenylene.

7. A metallocarborane chelate-antibody compound according to claim 1 wherein X is a radioisotope selected from the group consisting of $^{57}Co$, $^{99m}Tc$, $^{67}Cu$, $^{186}Re$ and $^{105}Rh$.

8. A metallacarborane chelate-antibody compound according to claim 1 wherein Y is 1,2-pyrazolylene.

9. A metallocarborane chelate-antibody compound according to claim 1 wherein X is $^{57}Co$ and Y is 1,2-phenylene.

10. A metallocarborane chelate-antibody compound according to claim 1 wherein X is $^{57}Co$ and Y is 1,2-pyrazolylene.

11. A composition for administration to animals comprising the metallacarborane chelate-antibody compound according to claim 1 and a pharmaceutically acceptable carrier.

* * * * *